United States Patent
Burks et al.

(10) Patent No.: US 10,301,928 B2
(45) Date of Patent: May 28, 2019

(54) MULTIPLE WELL ELEVATED TEMPERATURE COLUMN FLOW TESTING

(71) Applicant: Halliburton Energy Service, Inc., Houston, TX (US)

(72) Inventors: Jody M. Burks, Houston, TX (US); Ajish Sreeni Radhakrishnan Potty, Houston, TX (US); Zheng Lu, Kingwood, TX (US)

(73) Assignee: Halliburton Energy Services, Inc., Houston, TX (US)

(*) Notice: Subject to any disclaimer, the term of this patent is extended or adjusted under 35 U.S.C. 154(b) by 0 days.

(21) Appl. No.: 15/036,627

(22) PCT Filed: Aug. 20, 2014

(86) PCT No.: PCT/US2014/051893
§ 371 (c)(1),
(2) Date: May 13, 2016

(87) PCT Pub. No.: WO2015/147904
PCT Pub. Date: Oct. 1, 2015

(65) Prior Publication Data

US 2017/0218751 A1    Aug. 3, 2017

Related U.S. Application Data (63) Continuation-in-part of application No. PCT/US2014/032262, filed on Mar. 28, 2014.

(51) Int. Cl.
*G01N 11/06* (2006.01)
*E21B 47/10* (2012.01)
*G01N 33/28* (2006.01)

(52) U.S. Cl.
CPC .............. *E21B 47/10* (2013.01); *G01N 11/06* (2013.01); *G01N 33/2823* (2013.01)

(58) Field of Classification Search
None
See application file for complete search history.

(56) References Cited

U.S. PATENT DOCUMENTS 5,591,118 A    1/1997 Bierck
2002/0110925 A1    8/2002 Mansky et al.
(Continued)

FOREIGN PATENT DOCUMENTS

WO    WO-2013076242 A2    5/2013
WO    2015147880    10/2015
(Continued)

OTHER PUBLICATIONS

"International Application Serial No. PCT/US2014/051893, International Search Report dated Dec. 22, 2014", 3 pgs.
(Continued)

*Primary Examiner* — Jill E Culler
(74) *Attorney, Agent, or Firm* — Chamberlain Hrdlicka (57) ABSTRACT

A method of flow testing can include dispensing at least one solid material and at least one liquid into each of multiple wells in a filter plate, and then heating the filter plate with the solid material and liquid therein to an elevated temperature. A flow testing system can include a multiple well filter plate, each of the wells having disposed therein a selected combination of formation particles, a fracturing fluid and a liquid hydrocarbon, and a heating device that heats the filter plate to an elevated temperature.

20 Claims, 8 Drawing Sheets

(56) References Cited

U.S. PATENT DOCUMENTS

| | | | |
|---|---|---|---|
| 2008/0020944 A1 | 1/2008 | Anderson et al. | |
| 2010/0139914 A1 | 6/2010 | Tehrani et al. | |
| 2014/0319080 A1* | 10/2014 | Kaarigstad | G01N 33/2823 |
| | | | 210/774 |

FOREIGN PATENT DOCUMENTS

| | | |
|---|---|---|
| WO | WO-2015147904 A1 | 10/2015 |
| WO | WO-2015147905 A1 | 10/2015 |

OTHER PUBLICATIONS

"International Application Serial No. PCT/US2014/051893, Written Opinion dated Dec. 22, 2014", 7 pgs.

"International Application Serial No. PCT/US2014/051896, International Search Report dated Dec. 22, 2014", 3 pgs.

"International Application Serial No. PCT/US2014/051896, Written Opinion dated Dec. 22, 2014", 9 pgs.

Anonymous, "Swing Powerdose," Chemspeed Technologies, retrieved Oct. 11, 2018: pp. 1-3, <https://www.chemspeed.com/swing-powderdose/>.

Anonymous, "VolumeCheck 50 & 100 Factsheet," BioMicroLab, Inc., retrieved Sep. 28, 2018: pp. 1-2, <http://www.biomicrolab.com/volume-detection/volume-check>.

Anonymous, "VolumeCheck 100 Product Presentation," BioMicroLab, Inc., retrieved Sep. 28, 2018: pp. 1-22.

Penny et al., SPE 154308: "Nanofluid System Improves Post Frac Oil and Gas Recovery in Hydrocarbon Rich Gas Reservoirs," SPE International, 2012: pp. 1-18.

Penny et al., SPE 159692: "Laboratory and Field Evaluation of Proppants and Surfactants used in Fracturing of Hydrocarbon Rich Gas Reservoirs," SPE International, 2012: pp. 1-23.

\* cited by examiner

MULTIPLE WELL ELEVATED TEMPERATURE COLUMN FLOW TESTING

PRIORITY APPLICATIONS

This application is a U.S. National Stage Filing under 35 U.S.C. 371 from International Application No. PCT/US2014/051893, filed on 20 Aug. 2014, and published as WO 2015/147904 A1 on 1 Oct. 2015, which claims priority to PCT/US2014/032262 on 28 Mar. 2014, which applications and publication are incorporated herein by reference in their entirety.

TECHNICAL FIELD

This disclosure relates generally to equipment utilized and operations performed in conjunction with a subterranean well and, in one example described below, more particularly provides for column flow testing in which flow testing is performed at elevated temperature with multiple columns in a multiple well plate.

BACKGROUND

It can be useful to determine how readily fluids (such as, hydrocarbons, fracturing fluids, etc.) flow through earth formations and proppant. For example, selection of a fracturing fluid composition can be informed by knowledge of how various fracturing fluid compositions affect flow of hydrocarbons through earth formations and/or proppant. Therefore, it will be appreciated that improvements are continually needed in the art of flow testing.

DETAILED DESCRIPTION

Figure 1:
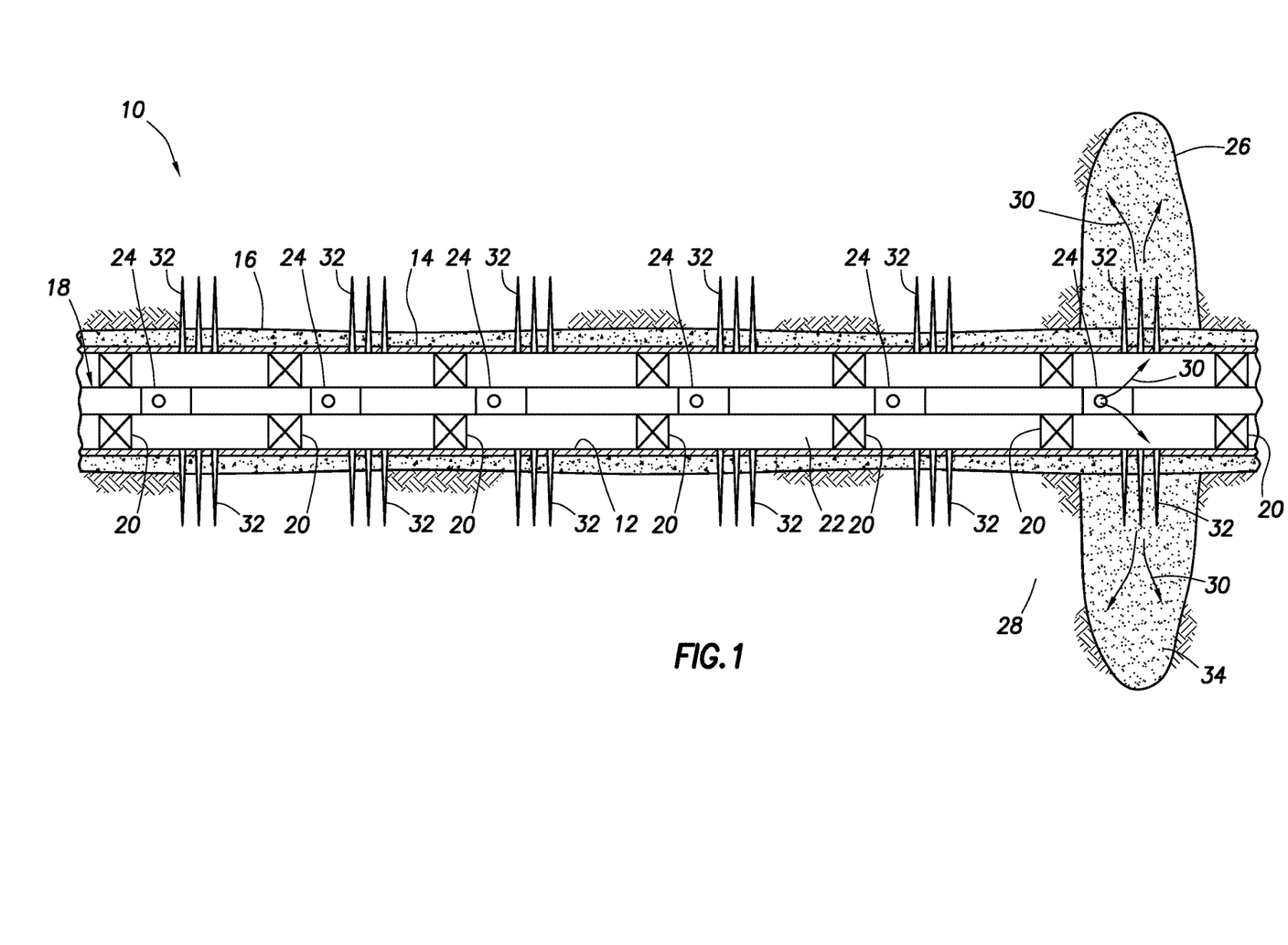
FIG. 1 is a representative partially cross-sectional view of a well system and associated method for which principles of this disclosure can be of use.

Representatively illustrated in FIG. 1 is a well system 10 and associated method which can benefit from the principles of this disclosure. However, it should be clearly understood that the system 10 and method are merely one example of an application of the principles of this disclosure in practice, and a wide variety of other examples are possible. Therefore, the scope of this disclosure is not limited at all to the details of the system 10 and method described herein and/or depicted in the drawings.

In the FIG. 1 system 10, a generally horizontal wellbore 12 is lined with casing 14 and cement 16. However, it should be clearly understood that it is not necessary for any particular wellbore section to be generally horizontal, or for the wellbore section to be cased or cemented.

In the FIG. 1 example, a generally tubular completion or stimulation string 18 is positioned in the wellbore 12 and packers 20 are set, to thereby isolate separate sections of an annulus 22 formed radially between the tubular string and the wellbore 12. Flow control devices 24 (such as, sliding sleeve valves, crossovers, specialized "frac" valves, etc.) selectively permit and prevent flow between an interior of the tubular string 18 and the annulus 22.

In other examples, the flow control devices 24 could be incorporated into the casing 12, packers 20 may not be used to isolate separate sections of the annulus 22, etc. Thus, it will be appreciated that the scope of this disclosure is not limited to use of any particular components, or combination of components, of the system 10 depicted in FIG. 1 or described herein.

A fracture 26 is formed in an earth formation 28 penetrated by the wellbore 12. The fracture 26 is formed by flowing pressurized fracturing fluid 30 outward from the tubular string 18, into the annulus 22 between an adjacent pair of the packers 20, and then into the formation 28 via perforations 32 formed through the casing 14 and cement 16.

Although only one fracture 26 is depicted in FIG. 1, multiple fractures can be formed at multiple locations along the wellbore 12 by, for example, selectively opening the flow control devices 24 and flowing the fracturing fluid 30 into the formation 28. The multiple locations can correspond to multiple different zones of the formation 28, or they can correspond to different formations or lithologies penetrated by the wellbore 12. Different fracturing fluid 30 compositions may be used at the different fracture locations along the wellbore 12.

Proppant 34 can be flowed into the fracture 26 along with the fracturing fluid 30, in order to prop the fracture open after it has been formed. The proppant 34 can serve purposes in addition to propping the fracture 26 open, such as, serving as a filter to prevent production of formation fines.

The proppant 34 can be a naturally-occurring substance (such as, sand), or a manufactured or synthesized substance (such as, glass beads, polymer spheres or fibers, etc.). Thus, the scope of this disclosure is not limited to any particular purpose or composition of the proppant 34 and, indeed, is not limited to use of any proppant at all.

It is desired, in this example, to determine how the fracturing fluid 30 flowed into the formation 28 affects subsequent flow of fluids (such as, formation water and formation hydrocarbons) through the formation and the proppant 34. In addition, it is desired to determine how the fracturing fluid 30 itself flows through the formation 28 and the proppant 34. In this way, an intelligent choice can be made as to a particular composition of the fracturing fluid 30 to use for each formation 28 or zone to be fractured.

The fracturing fluid 30 can be a combination of a variety of different components. For example, the fracturing fluid 30 can include water, a surfactant, a gel, a biocide, a clay stabilizer, a gel breaker, and/or other components. These components can be combined in various ratios. Thus, it will be appreciated that it would be very time-consuming to individually test each possible fracturing fluid 30 composition to determine its suitability for use with each formation 28 lithology and mineralogy, each proppant 34, each formation fluid, etc.

Instead, examples of systems and methods described herein allow for simultaneously flow testing a large number of fracturing fluid, formation, proppant and/or formation fluid combinations, so that informed decisions regarding choice of fracturing fluid composition can be made relatively rapidly. In addition, these systems and methods can be readily computer-controlled and automated, so that pertinent flow test results can be quickly made available to decision-makers, and possibilities for human error are minimized.

Furthermore, the systems and methods provide for performing flow tests at elevated temperatures to thereby more accurately simulate downhole conditions and to enhance mobility of more viscous hydrocarbons in some examples. As used herein, the term "elevated temperature" is used to indicate greater than ambient temperature. In some examples, the elevated temperature can correspond to a downhole temperature, such as, in the formation 28 where the fracture 26 is to be formed.

Figure 2:
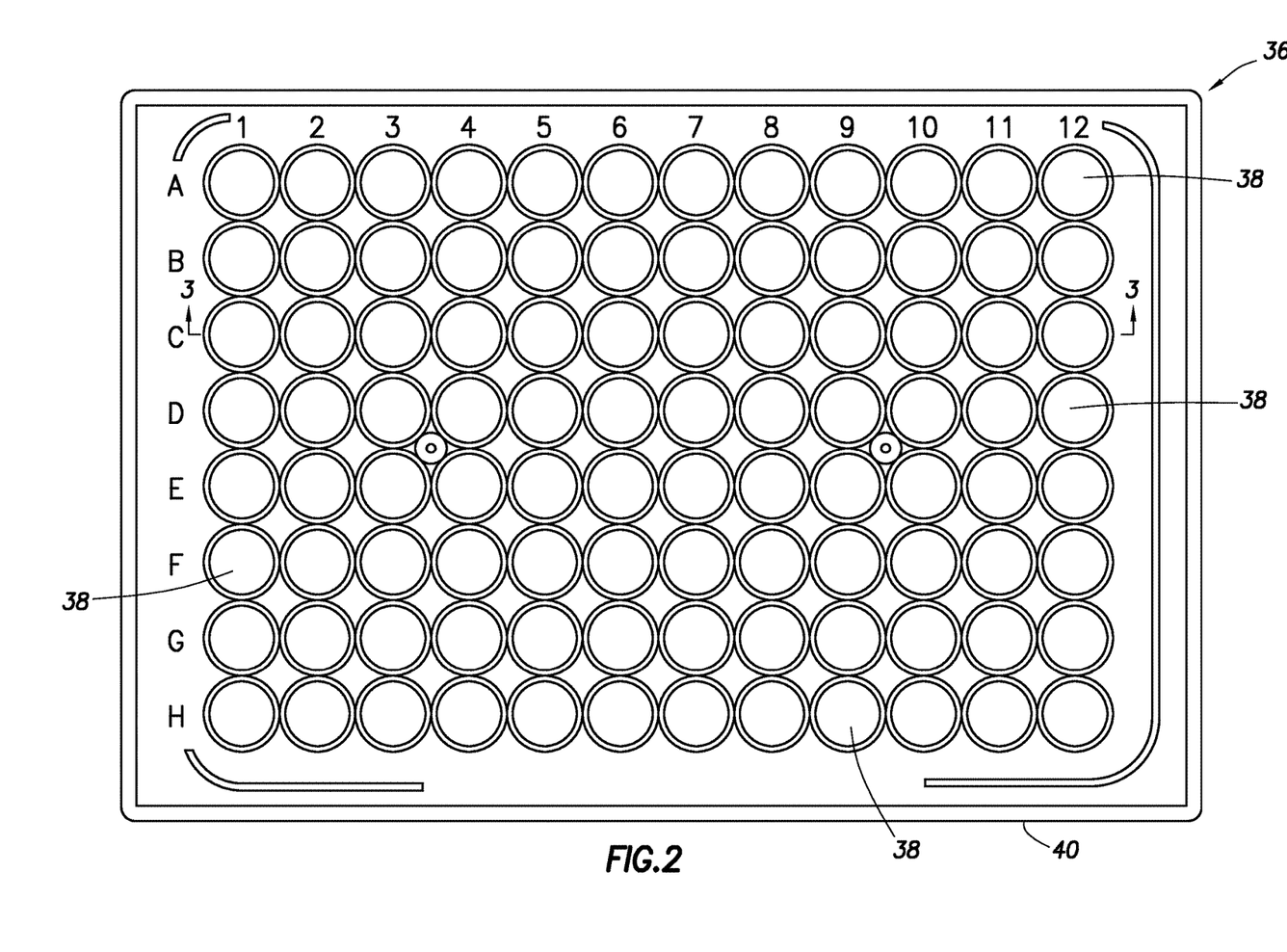
FIG. 2 is a representative top view of an example of a multiple well filter plate that can be used in systems and methods embodying the principles of this disclosure.

Referring additionally now to FIG. 2, an example of a filter plate 36 that can be used in systems and methods described below is representatively illustrated. A top view of the filter plate 36 is depicted in FIG. 2.

In the FIG. 2 example, the filter plate 36 includes ninety-six wells 38 arranged in eight rows and twelve columns. In other examples, six, twenty-four or more than a hundred wells 38 could be included in the filter plate 36. Thus, it should be clearly understood that the scope of this disclosure is not limited to use of any particular number of wells in a filter plate.

The wells 38 comprise receptacles for various formation solids, proppants, formation fluids, flowback water, fracturing fluids, etc., to be flow tested. In this manner, a large number and variety of different combinations and ratios can be simultaneously tested.

For example, using the filter plate 36 with ninety-six wells 38 as depicted in FIG. 2, each well could be loaded with the same formation particles (e.g., cuttings retrieved while the formation is being drilled) and/or proppant, and twelve different fracturing fluid compositions (e.g., with different surfactants or surfactant ratios, and with a zero surfactant control) could be flow tested with eight repetitions on the same plate to identify an optimal surfactant or surfactant ratio. As another example, each well 38 could be loaded with the same formation particles and/or proppant, and ninety-six different combinations of two or more surfactants in a blend could be flow tested on the same plate. As another example, each well 38 could be loaded with the same formation particles and/or proppant, and ninety-six different combinations of two or more surfactant blends could be flow tested on the same plate. As yet another example, each well 38 could be loaded with the same formation particles and/or proppant, and ninety-six different combinations of fracturing fluid components could be flow tested to identify detrimental factors (such as, incompatibilities between components that may or may not depend on the specific mineralogy of the formation).

Thus, it will be appreciated that a variety of different combinations can be simultaneously tested using the filter plate 36 with multiple wells 38. Note that the wells 38 can be integrally formed with a support structure 40 of the filter plate 36, or the wells could be separable from the support structure.

Figure 3:
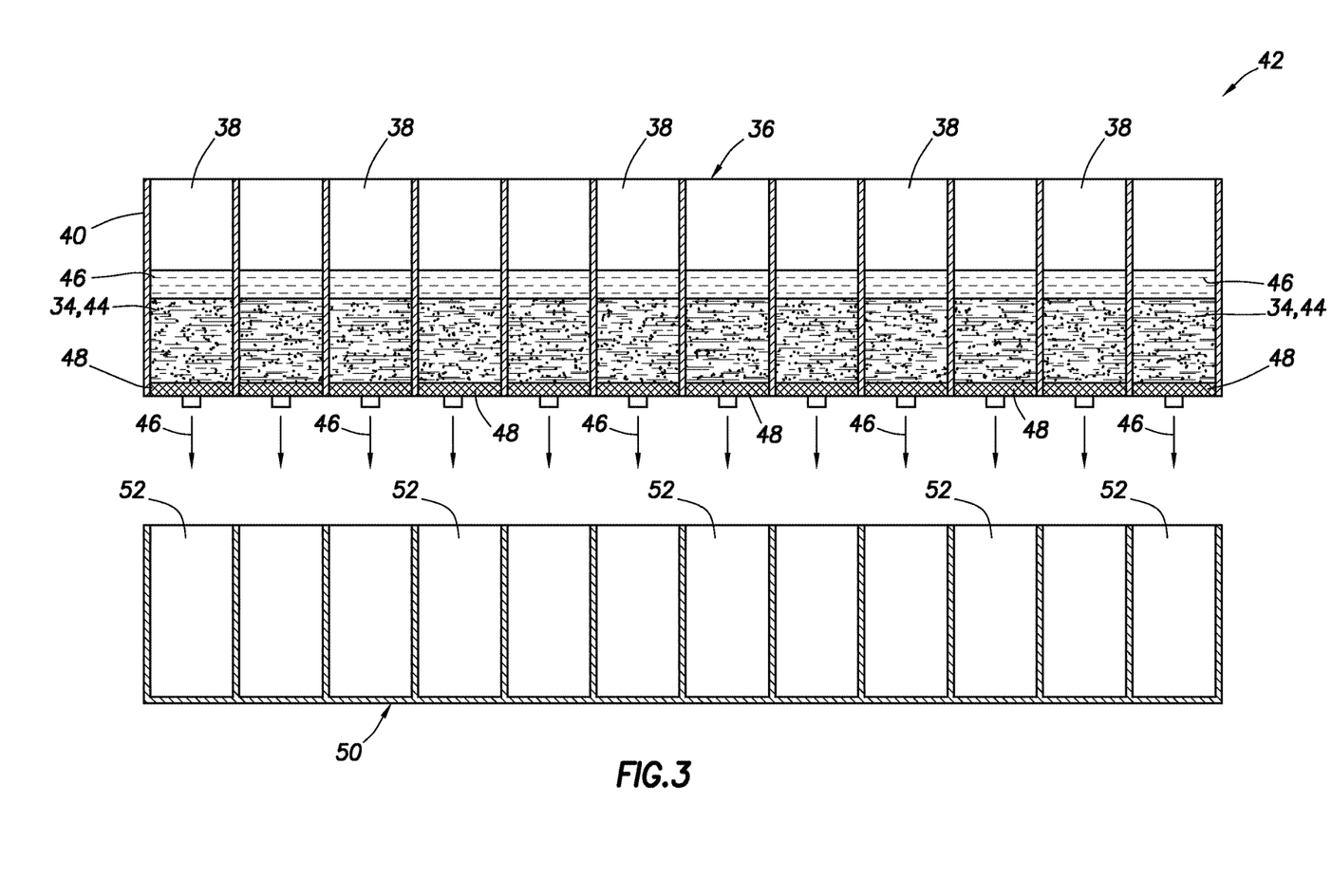
FIG. 3 is a representative cross-sectional view of the multiple well filter plate of FIG. 2, taken along line 3-3 of FIG. 2, along with a collection plate.

Referring additionally now to FIG. 3, a cross-sectional view of the filter plate 36 is representatively illustrated, taken along line 3-3 of FIG. 2. In this view, the filter plate 36 is depicted as being part of a flow testing system 42 that can embody the principles of this disclosure.

In some examples, the filter plate 36 can be heated to an elevated temperature, such as a downhole temperature. This heating step can be performed prior to loading the wells 38 with any solid material or liquid, that is, while the wells are empty. A hot block or other type of heating device may be used to heat the filter plate 36.

In the FIG. 3 example, a solid material (such as, formation particles 44 and/or proppant 34) and a liquid 46 (such as, formation water, flowback water or a 7% potassium chloride solution) are dispensed into each of the wells 38. In some examples, the solid material and/or the liquid 46 can be heated to an elevated temperature prior to being dispensed into the wells 38. This elevated temperature may be the same, or substantially the same, as the elevated temperature to which the filter plate 36 was previously heated.

Prior to loading the wells 38 with the solid material, a porous ceramic or screen 48 can be placed at a bottom of each well to prevent the solid material from falling out of the well. Optionally, prior to loading the wells 38 with the liquid 46, a sealing device 54 (such as, a sealing mat, PARA-FILM™, sealing tape or other sealing material, not shown in FIG. 3, see FIG. 4) can be used to prevent the liquid from flowing out of the wells.

The liquid 46 is allowed to flow through the solid material and into a collection plate 50. This flow can be by force of gravity, and/or the flow may be vacuum-assisted or by centrifugation. Once the liquid 46 has completed flowing from the filter plate 36 to the collection plate 50, the filter plate 36 and columns of solid materials in the wells 38 are ready for further flow testing.

In some examples, the liquid 46 can comprise flowback water (e.g., produced fracturing fluid), in which case it may be useful for the collection plate 50 to include separate wells 52 corresponding to the respective wells 38 in the filter plate 36, so that a volume or mass of liquid flowed from each well 38 can be determined. In this manner, a volume or mass of the liquid 46 retained in each of the wells 38 can be determined.

Figure 4:
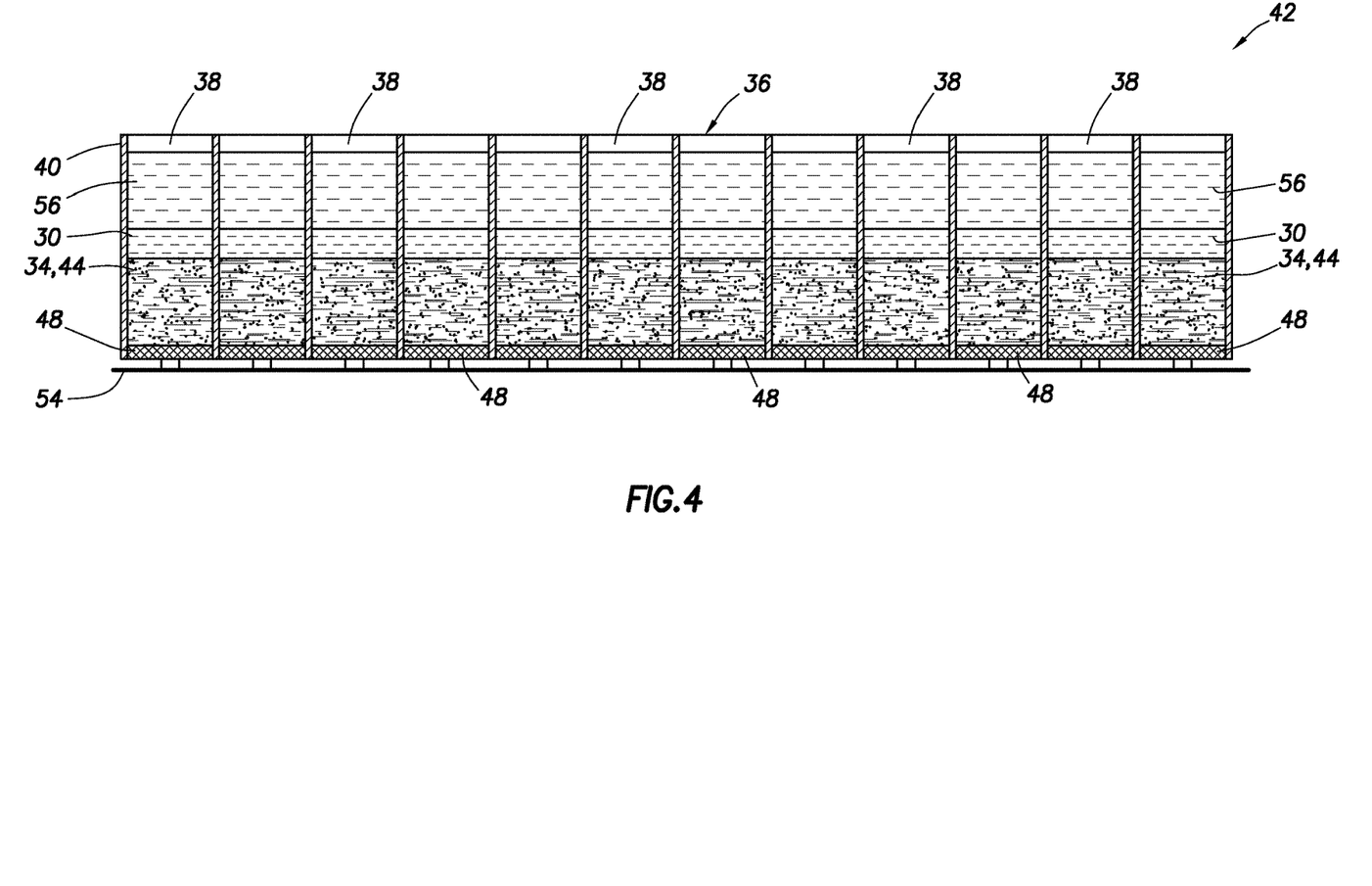
FIG. 4 is a representative cross-sectional view of the multiple well filter plate having solid materials and fluids loaded therein.

Referring additionally now to FIG. 4, the system 42 is representatively illustrated after additional liquids have been dispensed into the wells 38 in the filter plate 36. Prior to dispensing the additional liquids into the wells 38, the filter plate 36 can again be heated to an elevated temperature (which may be the same, or substantially the same, as the elevated temperature to which the filter plate was previously heated.

In some examples, the additional liquids may be heated to an elevated temperature prior to being dispensed into the wells 38. This elevated temperature may be the same, or substantially the same, as the elevated temperature to which the filter plate 36 was previously heated.

In the FIG. 4 example, fracturing fluid 30 and liquid formation hydrocarbons 56 (such as, crude oil, gas condensate, etc.) at the elevated temperature are dispensed into the wells 38. The sealing device 54 temporarily prevents the liquids from flowing out of the filter plate 36.

In examples where multiple liquids are dispensed into the wells 38, the filter plate 36 can be heated to the elevated temperature after each of the liquids is dispensed into the wells. Thus, in the FIG. 4 example, the filter plate 36 may be heated after the fracturing fluid 30 is dispensed into the wells 38, and the filter plate may be again heated after the liquid hydrocarbons 56 are dispensed into the wells.

Figure 5:
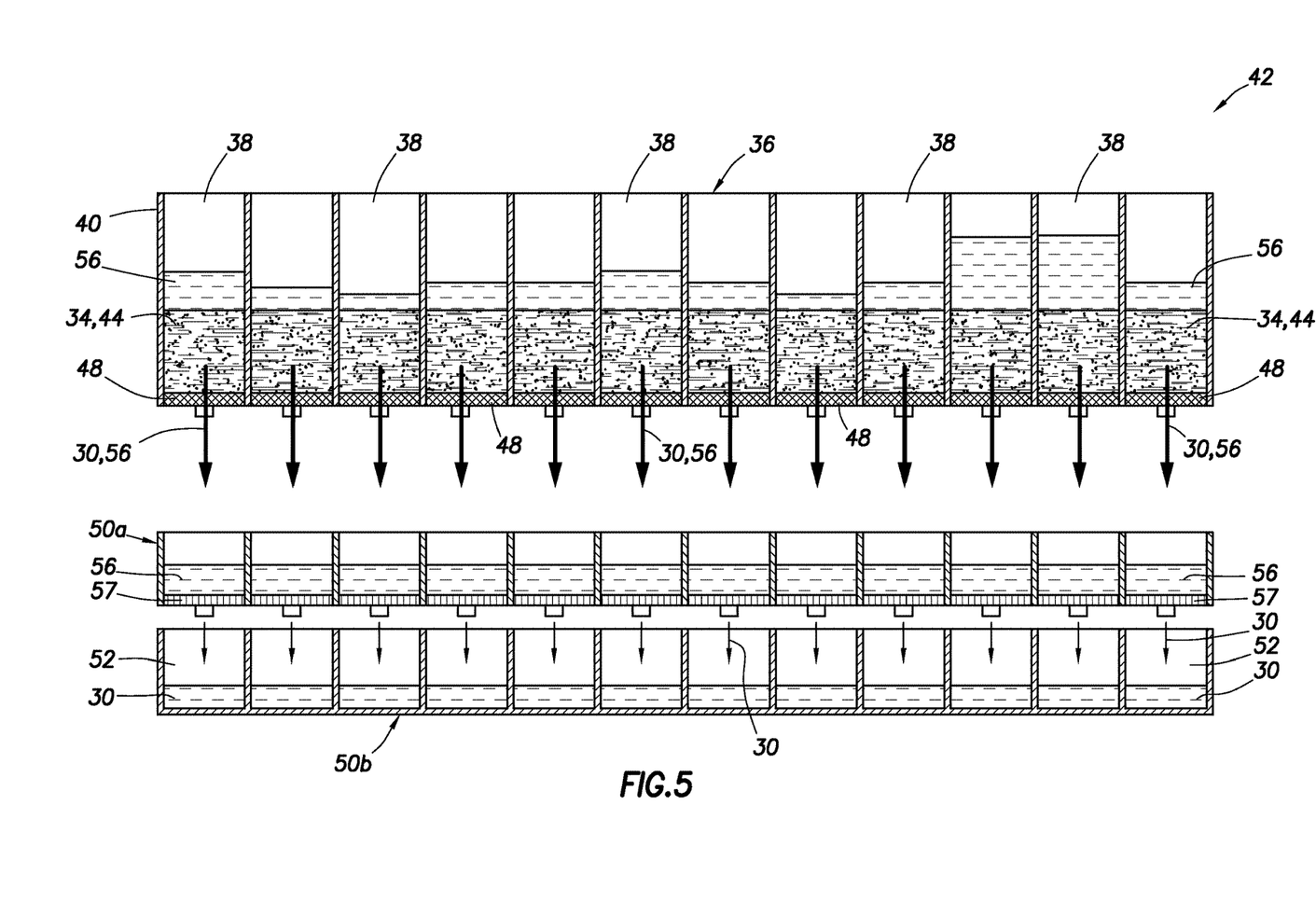
FIG. 5 is a representative cross-sectional view of the multiple well filter plate during a flow test.

Referring additionally now to FIG. 5, the system 42 is representatively illustrated after the sealing device 54 has been removed. The liquids (in this example, fracturing fluid 30 and formation hydrocarbons 56) are now allowed to flow from the filter plate 36 to collection plates 50a,b.

In this example, the liquids can flow from the filter plate 36 by force of gravity, or vacuum or centrifugation can be used to assist with the flow of the liquids. Although the plates 36, 50a,b are depicted in FIG. 5 as being separated, they would in a typical example be assembled into a stack during the flow of liquids from the filter plate 36. In addition, the plates 36, 50a,b may be heated to an elevated temperature during the flow of liquids from the filter plate 36.

The multiple collection plates 50a,b allow separation of the fracturing fluid 30 from the hydrocarbons 56 after they have been flowed from the filter plate 36. For example, a hydrophilic layer 57 can be used to permit aqueous substances (such as the fracturing fluid 30, formation water, etc.) to pass through to the lower collection plate 50b, while retaining the hydrocarbons 56 in the upper collection plate 50a. A hydrophobic layer could instead be used to retain the fracturing fluid 30 or other aqueous substance in the upper collection plate 50a, while allowing the hydrocarbons 56 to pass through to the lower collection plate 50b. However, the scope of this disclosure is not limited to use of multiple collection plates (for example, the single collection plate 50 depicted in FIG. 3 could be used instead) to collect non-separated fluids.

Figure 6:
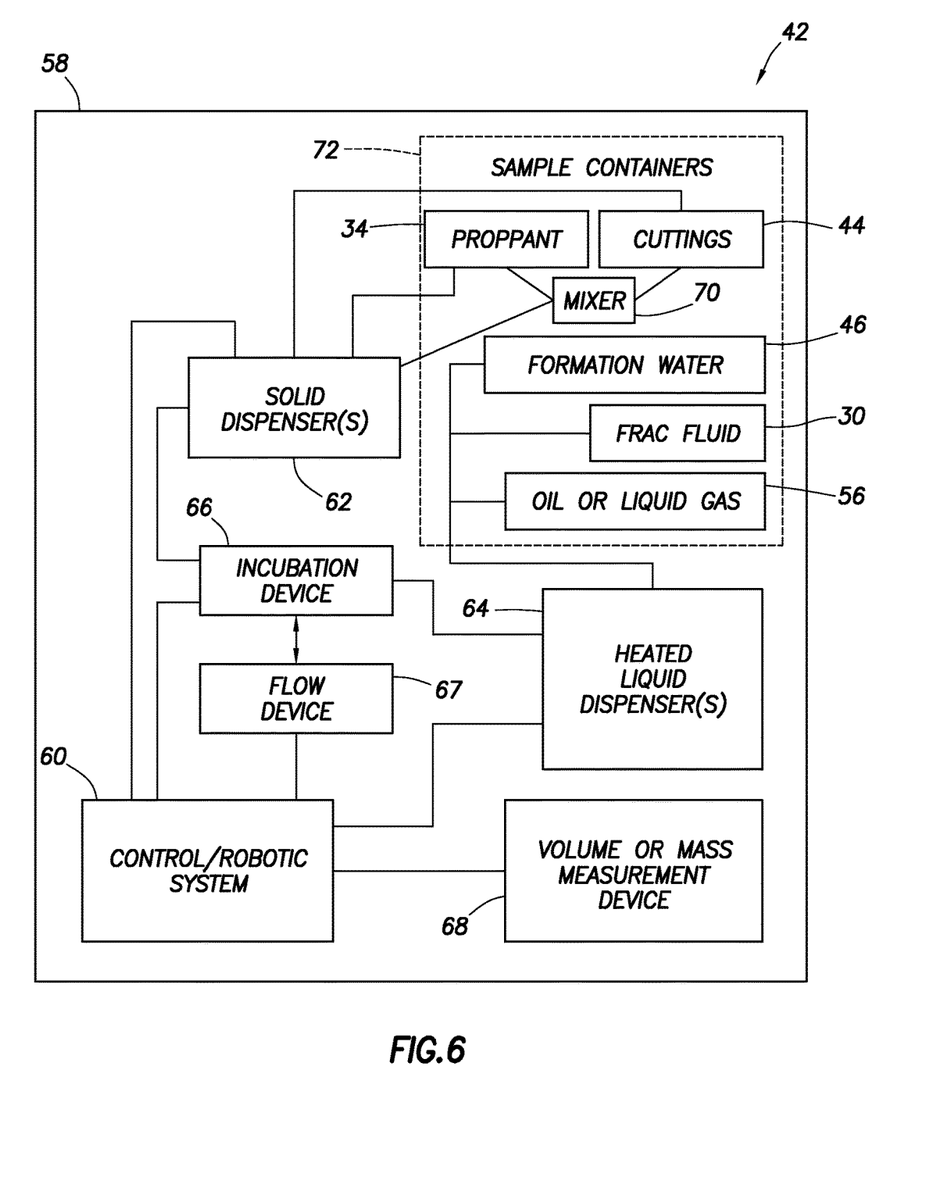
FIG. 6 is a representative block diagram of an example flow testing system that can embody the principles of this disclosure.

Referring additionally now to FIG. 6, a block diagram of one example of the system 42 is representatively illustrated. In this example, various components of the system 42 are contained in a single enclosure 58 for convenient transport, installation, operation, etc. However, in other examples, the components of the system 42 may not be contained in a single enclosure, and external devices (such as, input devices, monitors, printers, storage devices, etc.) may be included in the system. Thus, the scope of this disclosure is not limited to the details of the system 42 example as depicted in FIG. 6 or described herein.

In the FIG. 6 example, the system 42 includes a control system 60 that can be used to control operation of various robotic or automated devices of the system. For example, the system 42 can include one or more solids dispensers 62 and/or one or more liquids dispensers 64 that are capable of dispensing the solid materials (such as, formation particles 44 and proppant 34) and liquids (such as, liquid 46, fracturing fluid 30, and hydrocarbons 56) in selected combinations and ratios into the wells 38 of the filter plate 36 (not shown in FIG. 6, see FIG. 2).

The FIG. 6 example of the system 42 also includes an automated incubation device 66 for containing, heating and manipulating the filter plate 36 and collection plate 50 or collection plates 50a,b. Multiple plate stacks can be contained, heated and manipulated by the incubation device 66 in some examples.

Also included in the FIG. 6 system is a flow device 67 for containing the plate stacks during flow tests. The flow device 67 may also heat the plate stacks during flow tests. The incubation device 66 and the flow device 67 can be integrated into a single apparatus in some examples.

The FIG. 6 example of the system 42 also includes an automated volume or mass measurement device 68. The device 68 is used to measure a volume and/or mass of liquids collected in each well 52 of the collection plate 50 or collection plates 50a,b (not shown in FIG. 6, see FIGS. 3 & 5). The system 42 can also include an automated analytical or detection device (such as but not limited to, an automated UV-VIS spectrometer) for determining whether formation hydrocarbons 56 are present in any of the wells 52.

A mixer 70 may be used to mix the solid materials prior to the dispenser 62 dispensing the solid materials into the filter plate 36. The mixer 70 could be integrated with the dispenser 62 into a single apparatus. However, in some examples, mixing of solid materials may be unnecessary or undesired.

Suitable automated robotic solids and liquids dispensing equipment is available from Chemspeed Technologies of Switzerland, and North Brunswick, N.J. USA, and York, United Kingdom. Suitable automated ultrasonic liquid level detection equipment is available from BioMicroLab, Inc. of Concord, Calif. USA.

To aid in simulating downhole conditions for the flow tests, the entire system 42 or selected components thereof may be placed in an oven, or one or more heating devices (such as, a plate heater, hot block, heated dispensers 62, 64, etc.) can be incorporated into the system. In one example, sample containers 72 containing the various solid and liquid materials can be heated to downhole temperature prior to being dispensed into the filter plate 36, and the filter plate can be heated during incubation or at least prior to and/or during the flow tests, in order to ensure that all materials have equilibrated to downhole temperature.

Figure 7:
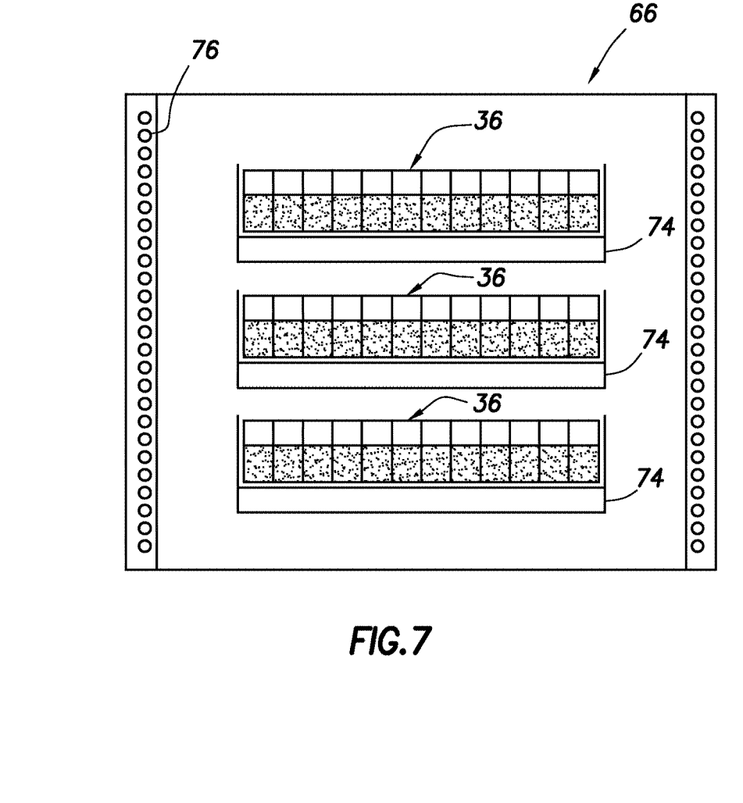
FIG. 7 is a representative view of an incubation/heater device that may be used in the flow testing system of FIG. 6.
Figure 8:
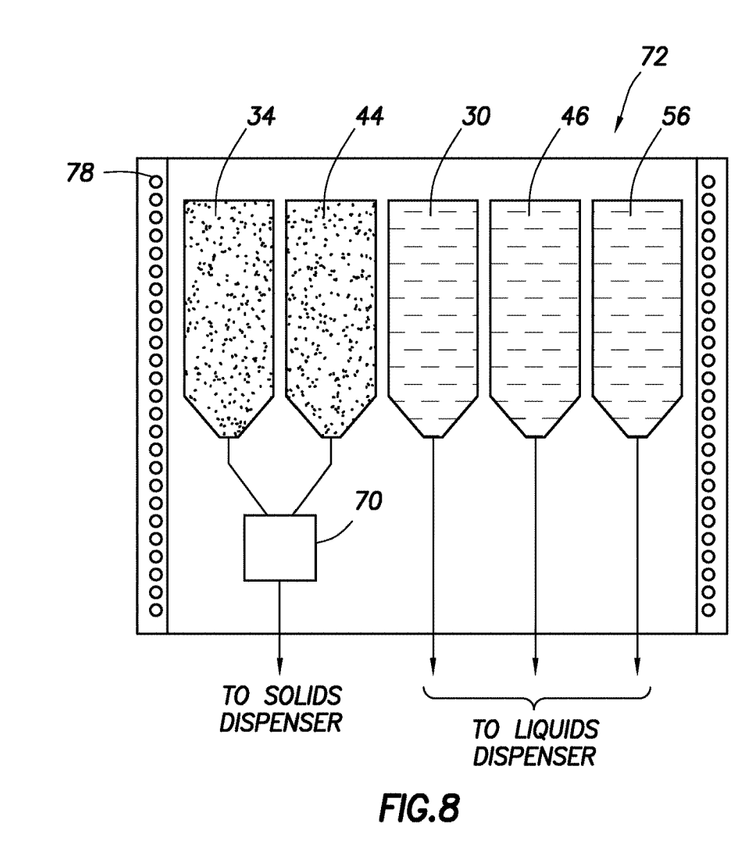
FIG. 8 is a representative view of heated sample containers that may be used in the flow testing system of FIG. 6.

The control system 60 controls operation of the dispensers 62, 64, the flow device 66, the measurement device 68 and any heating equipment (not shown in FIG. 6, see FIGS. 7 & 8). The control system 60 can include at least one processor, one or more types of memory, input and output devices, programmed instructions and/or other computer features.

It is contemplated that the system 42 could be sufficiently automated that an operator can simply load the sample containers 72 with appropriate solid and liquid materials, use an input device (not shown) to input various pertinent parameters (such as, downhole temperature or another elevated temperature, types of tests to be performed, etc.), and the system can then perform the tests without further human intervention, and return results for use by decision-makers. However, it should be clearly understood that the scope of this disclosure is not limited to only automated or robotic implementations, since one or more portions of the system 42 could be manually operated if desired.

Referring additionally now to FIG. 7, an example of the incubation device 66 is representatively illustrated. In this view, a manner in which the filter plate 36 (or a stack of plates) may be heated is depicted.

In the FIG. 7 example, multiple filter plates 36 having solid material(s) therein are being heated in the incubation device 66. However, it should be understood that the incubation device 66 may be used to heat one or more filter plates 36 when they are empty or after one or more solid materials and/or liquids are dispensed into the filter plates.

The incubation device 66 example depicted in FIG. 7 includes heating devices 74 (such as, hot blocks or plate heaters) for heating individual filter plates 36, as well as a heating device 76 (such as, a convection heater) for heating an entire interior space of the incubation device. Any combination of one or more heating devices, which individually or collectively heat one or more filter plates 36 or plate stacks may be used, in keeping with the scope of this disclosure.

Although not shown in FIG. 7, the incubation device 66 can include automated or robotic manipulating devices (such as, robotic arms, conveyors, etc.) for positioning the filter plates 36 or plate stacks in the incubation device, transferring the filter plates or plates stacks between the incubation device and the flow device 67, etc. In addition, as mentioned above, the incubation device 66 could be integrated with the flow device 67 in some examples.

Referring additionally now to FIG. 8, an example of the sample containers 72 is representatively illustrated. In this view, a manner in which the various solid materials and liquids may be heated in the system 42 can be seen.

In the FIG. 8 example, a heating device 78 (such as, a convection heater) is used to heat the proppant 34, formation particles 44, fracturing fluid 30, liquid 46 (such as, formation water, flowback water, potassium chloride solution, etc.) and formation hydrocarbons 56 to an elevated temperature (such as, a downhole temperature). Note that the mixer 70 is also depicted in FIG. 8 as being heated, so that as the solid materials are being mixed, their elevated temperature is maintained.

In other examples, the mixer 70 could be external to the sample containers 72 (such as, integrated with the solids dispenser 62. In some examples, the solids dispenser 62 and/or the liquids dispenser 64 may be heated (for example, similar to the manner in which the heating devices 76, 78 can be used to heat the incubation device 66 and the sample containers 72). Any types of heating devices (for example, radiant, convention, conduction, immersion, etc.) may be used, in keeping with the scope of this disclosure.

Figure 9:
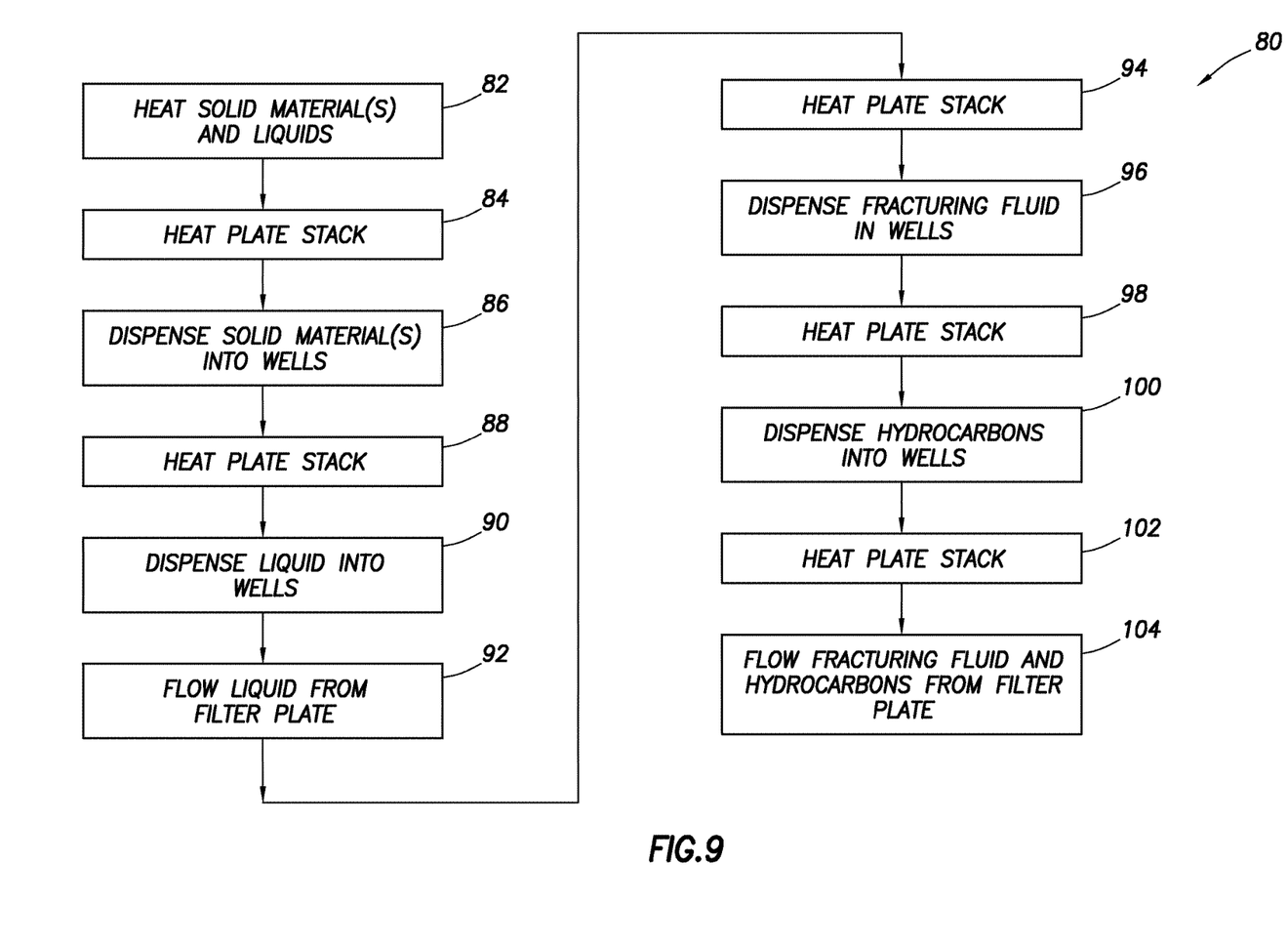
FIG. 9 is a representative flow chart for an example method that can embody the principles of this disclosure.

Referring additionally now to FIG. 9, an example of a flow testing method 80 that can embody the principles of this disclosure is representatively illustrated in flowchart form. The method 80 may be used with the system 42 examples described above, or the method may be used with other systems.

In step 82, one or more solid materials (such as, proppant 34 and formation particles 44) and one or more liquids (such as, fracturing fluid 30, liquid hydrocarbons 56 and other liquid 46 (for example, formation water, flowback water, potassium chloride solution, etc.)) are heated to an elevated temperature. The heating device 78 of FIG. 8 may be used to heat sample containers 72, or the solid materials and liquids may be separately heating, heated in another apparatus, etc. The scope of this disclosure is not limited to any particular technique or apparatus for heating solid materials or liquids.

In step 84, a plate stack (for example, including the filter plate 36 and the collection plate 50) is heated to an elevated temperature. For example, the heating device 74 and/or 76 may be used for heating the plate stack, or just the filter plate 36, to the elevated temperature in the incubation device 66.

In step 86, one or more solid materials are dispensed into the wells 38 of the filter plate 36. In the FIG. 9 example, a mixture of proppant 34 and formation particles 44 are dispensed into the wells 38 after having been heated in step 82, and after the plate stack is heated in step 84.

In other examples, however, only the proppant 34 or only the formation particles 44 may be dispensed into the wells 38, the proppant and formation particles may not be mixed, or the solid material and/or the filter plate 36 may not be heated prior to dispensing the solid material into the wells. The filter plate 36 may be centrifuged after the solid material is dispensed into the wells 38, if desired, to eliminate any voids in the solid material.

In step 88, the plate stack (or just the filter plate 36) is heated to an elevated temperature after the solid material(s) are dispensed into the wells 38 of the filter plate. The incubation device 66 may be used for this heating step. The elevated temperature in this step and in the other steps of the method 80 may be the same elevated temperature (such as, a downhole temperature), substantially the same elevated temperature, or different elevated temperatures may be used for different steps.

In step 90, one or more liquids are dispensed into the wells 38 of the filter plate 36. In the FIG. 9 example, the liquid 46 (such as, formation water, flowback water or potassium chloride solution) is dispensed into the wells 38 after having been heated in step 82, and after the plate stack is heated in step 88. In other examples, however, the liquid 46 and/or the filter plate 36 may not be heated prior to dispensing the liquid into the wells 38.

In step 92, the liquid 46 is allowed to flow from the filter plate 36 to the collection plate 50 (see, for example, FIG. 3). The liquid 46 may flow by force of gravity alone, or the flow may be assisted by vacuum or centrifugation. The plate stack may be heated to an elevated temperature during this step (for example, using the incubation device 66 combined with the flow device 67).

In step 94, the plate stack (or at least the filter plate 36) is heated to an elevated temperature after the liquid 46 has flowed from the filter plate 36. In this step 94, the plate stack can include the filter plate 36 and another collection plate 50 (i.e., different from the collection plate used in the previous steps, or at least emptied and cleaned prior to step 94), or the plate stack can include multiple collection plates 50a,b (for example, as depicted in FIG. 5). The incubation device 66 can be used for heating the plate stack in this step 94.

In step 96, the fracturing fluid 30 is dispensed into the wells 38 of the filter plate 36. In this example, the fracturing fluid 30 is dispensed after having been heated in step 82, and after the plate stack has been heated in step 94. In other examples, however, the fracturing fluid 30 and/or the filter plate 36 may not be heated prior to dispensing the fracturing fluid into the wells 38.

In step 98, the plate stack (or at least the filter plate 36) is heated to an elevated temperature. The incubation device 66 may be used in this step 98 for heating the plate stack.

In step 100, liquid formation hydrocarbons 56 are dispensed into the wells 38 of the filter plate 36. In this example, the hydrocarbons 56 are dispensed after having been heated in step 82, and after the plate stack has been heated in step 98. In other examples, however, the hydrocarbons 56 and/or the filter plate 36 may not be heated prior to dispensing the hydrocarbons into the wells 38.

In step 102, the plate stack (or at least the filter plate 36) is heated to an elevated temperature. The incubation device 66 may be used in this step 102 for heating the plate stack. The elevated temperature in this step 102 can correspond to a downhole temperature (such as, a temperature at the formation 28 where the fracture 26 is to be formed), and may be the same, or substantially the same, as the elevated temperatures in any of the previous steps 82, 84, 88, 94, 98.

In step 104, the fracturing fluid 30 and hydrocarbons 56 are allowed to flow from the filter plate 36 to the collection plate 50 or collection plates 50a,b (see, for example, FIG. 5). The fracturing fluid 30 and hydrocarbons 56 may flow by force of gravity alone, or the flow may be assisted by vacuum or centrifugation. The plate stack may be heated to an elevated temperature during this step (for example, using the incubation device 66 combined with the flow device 67).

Thus, the solid materials, liquids, combinations thereof and plates can be heated to an elevated temperature throughout the entire method 80, or at any points during the method (such as, before and/or during the flow steps 92, 104). Use of the elevated temperature in the method 80 can help to simulate downhole conditions, enhance mobility of viscous hydrocarbons, or for other purposes.

It may now be fully appreciated that the above disclosure provides significant advances to the art of column flow testing. In examples described above, fracturing fluid 30 selection (including components such as surfactants, gels, biocides, clay stabilizers, gel breakers, etc., and combinations and ratios thereof) can be optimized for use with a particular formation 28 and/or proppant 34, and this optimization can be performed relatively quickly, efficiently and accurately using the flow testing system 42 at elevated temperature.

In particular, the above disclosure provides to the art a method 80 of flow testing. In one example, the method 80 can comprise: dispensing at least one solid material (such as, the proppant 34 and/or the formation particles 44) and at least one liquid (such as, liquid 46 and/or fracturing fluid 30) into each of multiple wells 38 in a filter plate 36; and then heating the filter plate with the solid material and liquid therein to a first elevated temperature.

The method 80 can include heating the filter plate 36 prior to the dispensing step.

The method 80 can include heating the solid material 34, 44 prior to the dispensing step. The step of heating the solid material 34, 44 may include heating the solid material to substantially the first elevated temperature.

The method 80 can include heating the liquid 46 prior to the dispensing step. The step of heating the liquid 46 may include heating the liquid 46 to substantially the first elevated temperature.

The method 80 can include allowing the liquid 46 to flow from the filter plate 36, and then heating the filter plate 36.

The method 80 can include dispensing fracturing fluid 30 into the wells 38 after the step of allowing the liquid 46 to flow from the filter plate 36. The method 80 may include heating the filter plate 36 after the step of dispensing the fracturing fluid 30.

The method 80 can include dispensing liquid hydrocarbon 56 into the wells 38 after the step of heating the filter plate 36 after the step of dispensing the fracturing fluid 30. The method 80 may include heating the filter plate 36 after the step of dispensing the liquid hydrocarbon.

The method 80 can include allowing the fracturing fluid 30 and the liquid hydrocarbon 56 to flow from the filter plate 36, after the step of heating the filter plate 36 after the dispensing of the liquid hydrocarbon 56.

During the step of allowing the fracturing fluid 30 and the liquid hydrocarbon 56 to flow from the filter plate 36, the fracturing fluid and the liquid hydrocarbon may be at a second elevated temperature. The first and second elevated temperatures can be substantially equal.

The method can include selecting a composition of the fracturing fluid 30 for use in a well, after the step of allowing the fracturing fluid 30 and the liquid hydrocarbon 56 to flow from the filter plate 36.

A flow testing system 42 is also provided to the art by the above disclosure. In one example, the system 42 can comprise: a multiple well filter plate 36, each of the wells 38 having disposed therein a selected combination of formation particles 44, a fracturing fluid 30 and a liquid hydrocarbon 56; and a first heating device 74 and/or 76 that heats the filter plate 36 to an elevated temperature.

The system 42 may also include a second heating device 78 that heats one or more sample containers 72. The second heating device 78 may heat the sample containers 72 to substantially the same elevated temperature as the first heating device 74, 76 heats the filter plate 36.

The second heating device 78 may heat the fracturing fluid 30, the formation fluids 46, the liquid hydrocarbon 56, and/or the formation particles 44.

A composition of the fracturing fluid 30 can be selected for use in a well based on flow of the fracturing fluid 30 and the liquid hydrocarbon 56 through the formation particles 44.

Although various examples have been described above, with each example having certain features, it should be understood that it is not necessary for a particular feature of one example to be used exclusively with that example. Instead, any of the features described above and/or depicted in the drawings can be combined with any of the examples, in addition to or in substitution for any of the other features of those examples. One example's features are not mutually exclusive to another example's features. Instead, the scope of this disclosure encompasses any combination of any of the features.

Although each example described above includes a certain combination of features, it should be understood that it is not necessary for all features of an example to be used. Instead, any of the features described above can be used, without any other particular feature or features also being used.

It should be understood that the various embodiments described herein may be utilized in various orientations, such as inclined, inverted, horizontal, vertical, etc., and in various configurations, without departing from the principles of this disclosure. The embodiments are described merely as examples of useful applications of the principles of the disclosure, which is not limited to any specific details of these embodiments.

In the above description of the representative examples, directional terms (such as "above," "below," "upper," "lower," etc.) are used for convenience in referring to the accompanying drawings. However, it should be clearly understood that the scope of this disclosure is not limited to any particular directions described herein.

The terms "including," "includes," "comprising," "comprises," and similar terms are used in a non-limiting sense in this specification. For example, if a system, method, apparatus, device, etc., is described as "including" a certain feature or element, the system, method, apparatus, device, etc., can include that feature or element, and can also include other features or elements. Similarly, the term "comprises" is considered to mean "comprises, but is not limited to."

Of course, a person skilled in the art would, upon a careful consideration of the above description of representative embodiments of the disclosure, readily appreciate that many modifications, additions, substitutions, deletions, and other changes may be made to the specific embodiments, and such changes are contemplated by the principles of this disclosure. For example, structures disclosed as being separately formed can, in other examples, be integrally formed and vice versa. Accordingly, the foregoing detailed description is to be clearly understood as being given by way of illustration and example only, the spirit and scope of the invention being limited solely by the appended claims and their equivalents.

What is claimed is:

1. A method of flow testing, comprising:
dispensing a solid material and a liquid into each well of a multiple well filter plate, wherein each liquid comprises hydrocarbons and a fracturing fluid composition and at least two wells of the multiple wells contain different fracturing fluid compositions;
heating the filter plate with the solid material and liquid therein to a first elevated temperature;

flowing each of the liquids through the filter plate via gravity, vacuum assistance, or centrifugation;

measuring at least one of a volume of each of the liquids flowed through the filter plate or a mass of each of the liquid flowed through the filter plate;

determining if hydrocarbons are present in any of the liquids flowed through the filter plate; and selecting one of the fracturing fluid compositions for use in a subterranean well fracturing operation based on at least one of the presence of hydrocarbons in the liquids flowed through the filter plate, volume measurements of the liquids flowed through the filter plate, or mass measurements of the liquids flowed through the filter plate.

2. The method of claim 1, further comprising heating the filter plate prior to the dispensing.

3. The method of claim 1, further comprising heating the solid material prior to the dispensing.

4. The method of claim 3, wherein the heating the solid material comprises heating the solid material to substantially the first elevated temperature.

5. The method of claim 1, further comprising heating the liquids prior to the dispensing.

6. The method of claim 5, wherein the heating the liquids comprises heating the liquids to substantially the first elevated temperature.

7. The method of claim 1, further comprising heating the filter plate after flowing each of the liquids through the filter plate via gravity, vacuum assistance, or centrifugation.

8. The method of claim 7, further comprising flowing at least one of the group consisting of formation water and potassium chloride solution through the solid material, after the solid material is dispensed into the wells and before the liquids are dispensed into the wells.

9. The method of claim 8, further comprising heating the filter plate after the dispensing of each of the liquids.

10. The method of claim 9, further comprising dispensing liquid hydrocarbon into the wells after the heating the filter plate after the dispensing of each of the liquids.

11. The method of claim 10, further comprising heating the filter plate after the dispensing of the liquid hydrocarbon.

12. The method of claim 11, wherein flowing each of the liquids through the filter plate via gravity, vacuum assistance, or centrifugation further comprises allowing the liquid hydrocarbon to flow from the filter plate, after the heating of the filter plate after the dispensing of the liquid hydrocarbon.

13. The method of claim 12, wherein during the allowing the liquid hydrocarbon to flow from the filter plate, each of the liquids and the liquid hydrocarbon are at a second elevated temperature.

14. The method of claim 13, wherein the first and second elevated temperatures are substantially equal.

15. A flow testing system, comprising:
a multiple well filter plate, each of the wells having disposed therein a selected combination of formation particles, fracturing fluids, and a liquid hydrocarbon, wherein at least two wells of the multiple well filter plate contain different fracturing fluids;
a collection plate, wherein the fracturing fluid composition and the liquid hydrocarbon flow from the filter plate to the collection plate, wherein the fracturing fluid composition and the liquid hydrocarbon flow from the filter plate to the collection plate via gravity, vacuum assistance, or centrifugation;
a detection device configured to determine if any hydrocarbons are present in the collection plate; and
a first heating device that heats the filter plate to an elevated temperature.

16. The system of claim 15, further comprising a second heating device that heats at least one sample container.

17. The system of claim 16, wherein the second heating device heats the sample container to substantially the same elevated temperature as the first heating device heats the filter plate.

18. The system of claim 16, wherein the second heating device heats the fracturing fluid.

19. The system of claim 16, wherein the second heating device heats the liquid hydrocarbon.

20. The system of claim 16, wherein the second heating device heats the formation particles.

* * * * *